United States Patent [19]

Holmes et al.

[11] Patent Number: 5,069,810

[45] Date of Patent: Dec. 3, 1991

[54] CLEANING COMPOSITION COMPRISING MICROBIAL LIPASE SD2 AND SODIUM DODECYLBENZENE SULFONATE

[75] Inventors: Paul E. Holmes, Hamden; Katherine P. Roberts, Derby; Christine M. August, Plainville, all of Conn.

[73] Assignee: Olin Corporation, Cheshire, Conn.

[21] Appl. No.: 428,550

[22] Filed: Oct. 30, 1989

Related U.S. Application Data

[63] Continuation-in-part of Ser. No. 324,062, Mar. 16, 1989.

[51] Int. Cl.$^5$ .................. C11D 3/386; C11D 1/24; C11D 7/42
[52] U.S. Cl. ........................ 252/174.12; 252/173; 252/558; 252/DIG. 12
[58] Field of Search .............. 252/174.12, DIG. 12, 252/558, 173; 435/264

[56] References Cited

U.S. PATENT DOCUMENTS 4,283,494  8/1981  Kokusho et al. .................. 435/198

FOREIGN PATENT DOCUMENTS 0214761  3/1987  European Pat. Off. .
8700859  3/1987  Int'l Pat. Institute .
8700859  2/1987  World Int. Prop. O. .

OTHER PUBLICATIONS

Article "Specific and Sensitive Plate Assay for Bacterial Lipases", by Gisela Kouker and Karl-Erich Jaeger, Jan. 1987, pp. 211-213.

*Primary Examiner*—Paul Lieberman
*Assistant Examiner*—A. Beadles-Hay
*Attorney, Agent, or Firm*—Dale Lynn Carlson

[57] ABSTRACT

This invention is directed to a detergent composition comprising the microbial lipase SD2 and dodecylbenzene sulfonate. In the detergent composition, the lipase SD2 is characterized by having (i) optimum pH for activity of about $8\pm0.5$; (ii) an optimum temperature for activity of about 30° to 55° C. and (iii) a molecular weight as measured by gel permeation chromatography of about $8.8\times10^4$.

6 Claims, No Drawings

CLEANING COMPOSITION COMPRISING MICROBIAL LIPASE SD2 AND SODIUM DODECYLBENZENE SULFONATE

This application is a continuation-in-part of co-pending U.S. application Ser. No. 07/324,062, filed on Mar. 16, 1989.

The invention herein described relates generally to a new detergent composition, and more particularly a composition suitable for use in laundry and/or dishwashing applications.

By way of background, dodecylbenzene sulfonate ("DBS") is a commonly used surfactant employed in household detergents. It is considered low-cost, safe and effective. Because of dodecylbenzene sulfonate's wide-spread usage in cleaning products, compatibility with and efficacy in the presence of this surfactant is an important consideration in the evaluation of new detergent additives.

Recently, lipases have become of interest as laundry detergent additives. By way of illustration, Novo Industri A/S has recently introduced into the marketplace a lipase referred to as LIPOLASE. However, the present inventors have found that LIPOLASE is not as effective as might be desired in performing its function of breaking down lipids into fatty acids, particularly in the presence of DBS when formulated into dodecylbenzene sulfonate-containing laundering formulations.

In view of the above, new lipases exhibiting enhanced efficacy in the presence of dodecylbenzene sulfonate would be highly desired by the detergent manufacturing community.

In one aspect, the present invention relates to a detergent composition comprising the microbial lipase SD2 and sodium dodecylbenzene sulfonate. In the detergent, the lipase is characterized by having (i) an optimum pH for activity of about 8±0.5; (ii) an optimum temperature for activity of about 30° to 55° C. and (iii) a molecular weight as measured by gel permeation chromatography of about $8.8 \times 10^4$. This and other aspects will become apparent from a reading of the following detailed specification.

The present inventors have isolated a biologically pure culture of a previously undescribed strain of *Pseudomas alcaligenes*, strain SD2, as disclosed and claimed in co-pending, commonly-assigned U.S. application Ser. No. 324,062, incorporated herein by reference in its entirety. The organism is a natural isolate and has been deposited with the American Type Culture Collection (ATCC), having been assigned the accession number ATCC 53877. This novel strain SD2 was found to produce a novel lipase.

The microorganism, *P. alcaligenes*, strain SD2, was isolated from a shower drain by direct isolation on a Tryptone-Soytone-Olive oil isolation medium. The isolation medium employed is more fully described in Table I below.

TABLE I

| Isolation Medium | Percent by Weight |
| --- | --- |
| Ammonium sulfate | 0.5 |
| Potassium phosphate, dibasic | 0.05 |
| Magnesium sulfate, heptahydrate | 0.025 |
| Tryptone (Difco) | 1.7 |
| Soytone (Difco) | 0.3 |
| Olive oil | 1.0 |
| Rhodamine B | 0.001 |

TABLE I-continued

| Isolation Medium | Percent by Weight |
| --- | --- |
| Agar | 1.5 |

The Rhodamine B dye in the isolation medium causes lipase-producing bacterial colonies to fluoresce an orange color when irradiated with long wavelength ultraviolet light (Kouker, G. and K. -E. Jaeger, 1987, *App. Environ. Microbiol*, 53: 211-3). This fluorescence permits the easy identification of lipase-producers. Colonies so identified were purified by restreaking onto similar media. Stock cultures were maintained on Difco TSA slants.

The bacterial isolate was identified using standard taxonomic procedures from *Bergey's Manual of Systematic Bacteriology* (Williams & Wilkins, Baltimore, 1984). The results of applicable physiological characterization tests of *P. alcaligenes* strain SD2 are presented in Table II and compared with characteristics of *P. alcaligenes* and *P. pseudoalicaligenes* published in Bergey's Manual.

TABLE II

Substrate Utilization of *P. alcaligenes* Strain SD2, *P. alcaligenes*, and *P. pseudoalicaligenes*

| | Strain* | | |
| --- | --- | --- | --- |
| | SD2 | *P. alcaligenes* | *P. pseudoalicaligenes* |
| Fructose | − | − | + |
| L-aspartate | + | − | − |
| L-glutamate | − | + | + |
| D-gluconate | − | − | d |
| L-Histidine | − | d | d |
| Ethanolamine | − | − | + |
| n-Butanol | − | d | + |
| Isobutanol | + | d | − |
| Citrate | − | d | d |
| Betaine | − | − | + |
| Glycerol | − | − | d |
| Sorbitol | − | − | d |
| Itaconate | − | − | d |

Abbreviation:
d (11-80 percent of strains positive);
+ (strain was able to utilize the indicated chemical for growth);
− (strain did not utilize the chemical for growth).
*Data for *P. alcaligenes* and *P. pseudoalicaligenes* are from Bergey's Manual of Systematic Bacteriology (Williams & Wilkins [Baltimore, 1984]).
Compounds utilized by all strains include: DL-lactate, succinate, fumarate, acetate, L-arginine, caprate, and L-malate.
Compounds not utilized by any strain include: D-glucose, L-arabinose, D-mannose, D-mannitol, L-rhamnose, D(+)-galactose, D(−)-ribose, m.-inositol, L-threonine, m-tartrate, adipate, phenylacetate, nicotinate, sebacate, suberate, benzoate, and pimelate.

This table illustrates nutritional capabilities of the indicated strains and further illustrates their differences.

Several lipase-producing strains of *P. pseudoalicaligenes* are disclosed in International Publication No. WO 87/00859 published under the Patent Cooperation Treaty. Table III presents certain morphological and physiological characteristics of *P. alcaligenes* strain SD2, as compared to the characteristics of four strains of *P. pseudoalicaligenes* disclosed in International Publication No. WO 87/00859. Differences between the SD2 strain of the present invention and the other strains are readily apparent. For example, SD2 utilized L-aspartate, while the two other Pseudomonas species did not, as noted noted in Table II.

TABLE III

Characteristics of *P. alcaligenes* Strain SD2 and Selected Lipase-Producing Strains of *P. pseudoalicaligenes*.
(The CBS Strain Accession Numbers Correspond to Those Referenced in International Publication No. WO 87/00859)

| Characteristic | Strain of Invention SD2 | Comparison Strains | | | |
|---|---|---|---|---|---|
| | | CBS 467.85 | CBS 468.85 | CBS 471.85 | CBS 473.85 |
| Cell shape | rod | rod | rod | rod | rod |
| Motility | + | + | + | + | + |
| Spores | − | − | − | − | − |
| Gram Strain | − | − | − | − | − |
| Oxidase | + | + | + | + | + |
| Anaerobic glucose | − | − | − | − | − |
| Aerobic glucose | − | − | − | − | − |
| Aerobic maltose | − | − | − | − | − |
| Aerobic sucrose | − | − | − | − | − |
| Aerobic D-xylose | − | − | − | − | + |
| Arginine dihydralase | + | + | + | − | + |
| Gelatin hydrolysis | − | − | − | − | − |
| Starch hydrolysis | − | − | − | − | − |
| $NO_3^- \rightarrow NO_2^-$ | + | + | + | + | + |
| $NO_2^- \rightarrow N_2$ | + | − | − | − | − |
| Citrate Utilization | − | + | + | + | + |
| Catalase | + | + | + | + | + |
| Growth at 41° C. | + | + | + | + | + |

Strain SD2 of the present invention can be grown in various types of culture media under conditions suitable for growth of pseudomonads. Typically, such media contain assimilable sources of carbon, nitrogen, and various inorganic mineral nutrients. By way of illustration, *P. alcaligenes* strain SD2 was grown in L-Aspartate Medium having the formulation as shown in Table IV.

TABLE IV

| Culture Medium | |
|---|---|
| Ingredient | Percent by Weight |
| Ammonium sulfate | 0.5 |
| Potassium phosphate, dibasic | 0.05 |
| Magnesium sulfate, heptahydrate | 0.025 |
| Tris(hydroxymethyl)aminomethane | 1.21 |
| L-Aspartic acid | 2.0 |
| Brij ® 58 | 1.0 mM |
| FeCl$_3$ | 1.0 μM |

The medium is adjusted to pH 7.5–8.0 with potassium hydroxide prior to sterilization. The advantage of this medium over the Tryptone medium referred to in U.S. application Serial No. 324,062 is that a white product is obtained, free of colored high molecular weight metabolites typically found in Tryptone medium.

The lipase of the invention is found in culture media, preferably liquid media, containing *P. alcaligenes* strain SD2. Quantities of this enzyme can be obtained by culturing *P. alcaligenes* strain SD2 in liquid culture and under culture conditions suitable for growth of organisms of this type. For example, an actively growing broth culture of *P. alcaligenes* strain SD2 is suitably used as an inoculum and introduced into Erlenmeyer flasks containing L-Aspartate medium (C. F. Table IV). In addition, the inclusion of the non-ionic surfactant BRIJ ® 58 [polyoxyethylene (20) cetyl ether] in liquid growth medium containing *P. alcaligenes* strain SD2 at a 1–10 mM concentration, preferably 1 mM, increased the yield of the lipase by a factor of two-fold or more in contrast to control cultures without this surfactant. Cultures are incubated with shaking for about 24 hours at a temperature of about 30° C. Following this culture growth period, the bacterial cells are removed by centrifugation or filtration or other suitable techniques. The lipase which is found in the resultant clarified culture liquor is then generally concentrated prior to use. Several methods may be used to concentrate this enzyme, including ultrafiltration as discussed in Example 1.

It is desirable that lipases intended for commercial utilization be stable in the presence of various surfactants commonly found in cleaning product formulations. Advantageously, the lipase of *P. alcaligenes* strain SD2 was found to be functional in the presence of commercial surfactants such as dodecylbenzene sulfonate and fatty alcohol ethoxysulfates. In a laundry detergent composition the lipase strain SD2 is employed in an amount of between about one million and about 100 million, preferably between about 5 and about 10 million lipase units per kilogram of DBS in the detergent. Upon dilution of the detergent composition with water to form a wash solution, the lipase SD2 is generally present in an amount of between about one and about 500, preferably between about 3 and about 5 lipase units per milliliter of laundry wash solution. The term "lipase unit" is defined in Table V, footnote (1).

Regarding the stability of the lipase produced by *P. alcaligenes* strain SD2, this enzyme loses activity during storage at a rate that is directly proportional to temperature. For example, during accelerated aging tests conducted at a temperature of 37° C. and a pH of 7.0, the lipase useful in this invention demonstrated a half-life of about 5 days in the absence of surfactants. The addition of calcium, in the form of CaCl$_2$, stabilized the SD2 lipase and increased its half-life to over 45 days at suitable CaCl$_2$ concentrations. The concentration of CaCl$_2$ required to enhance such enzyme longevity is related to the particular lipase formulation. For example, in simple buffered enzyme solutions lacking surfactants, where the buffer is, for example, 50 mM BES [N, N-bis'(2-hydroxyethyl)-2-amino-ethanesulfonic acid] at pH 7.0, the addition of 5 mM CaCl$_2$, preferably 10 mM, is sufficient. The optimum concentration of CaCl$_2$ in the presence of preferred surfactants is about 25 mM or more. In formulations of the lipase of *P. alcaligenes* strain SD2, various surfactants can be used in view of this lipase's stability in the presence of surfactants. Examples of preferred surfactants include the non-ionic surfactant BRIJ ® 35 [polyoxyethylene (23) lauryl ether] and the anionic surfactant SANDOPAN ® DTC gel (sodium trideceth-7-carboxylate). Preferred non-ionic surfactants are those having a hydrophobic end containing 12–16 carbon units, and a polyoxyethylene chain size of about 20–23 ethylene oxide units. In general, anionic surfactants of the carboxylated type are preferred and are most compatible with the novel lipase of *P. alcaligenes* strain SD2.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

(A) Preparation of Lipase From *Pseudomonas alcaligenes* Strain SD2

The microorganism of the invention, *P. alcaligenes* SD2, was conveniently grown in the culture medium previously presented in Table IV.

A 50 mL starter culture of *P. alcaligenes* SD2 in a 250 mL Erlenmeyer flask was grown for about 16 hours at a temperature of 30° C. at 175 rpm on a gyratory shaker. This starter culture was then used to inoculate 8 liters of culture medium divided among 4 and 6 L fluted Erlenmeyer flasks such that no individual flask contained more than 25 percent flask capacity as liquid. The culture flasks thus prepared were incubated for 24 hours at a temperature of 30° C. with gyratory shaking at 150 rpm.

Following the culture period, the lipase of the invention was harvested and concentrated by first removing the bacterial cells from the 8 liters of liquid culture by tangential flow filtration using Pharmacia $10^6$ (NMWC) Omega membrane cassettes. The resultant cell-free filtrate was then concentrated by tangential flow ultrafiltration using Pharmacia 30,000 (NMWC) Omega membrane cassettes. Thereafter, the concentrate was diafiltered at 3° C. with about 10 volumes of 50 mM BES, pH 7.0, supplemented with 10 mM $CaCl_2$ in order to eliminate all low molecular weight contaminants (those with molecular weights less than or equal to 30,000), and to change the lipase solvent to one with buffer and stabilizing $CaCl_2$. The yields of enzyme from three separate batch cultures are presented in Table V.

TABLE V

| Yields of Lipase Produced by Cultures of *P. alcaligenes* Strain SD2 | | |
|---|---|---|
| Batch No. | Units/mL[1] | Total Units |
| 20 | 39.15 | 10,571 |
| 21 | 34.69 | 7,840 |
| 22 | 37.41 | 6,172 |

[1]One unit is the amount of lipase which produces one microequivalent of fatty acid from olive oil per minute at 37° C. and at pH 10.

(B) Production of the Lipase *P. alcaligenes* Strain SD2 and Molecular Weight Measurement Quantities of the lipase of *P. alcaligenes* strain SD2 were obtained by culturing of the organism in the medium of Table IV, removing the bacterial cells by filtration, concentrating the enzyme by ultrafiltration as already described. Lipolytic activity was assayed using the following standard composition: (i) 2.5 mL substrate [10 percent (w/v) olive oil emulsified in 10 percent (w/v) gum arabic]; (ii) 2.0 mL buffer [1.0M CHES (2[N-cyclohexylamino]-ethane sulfonic acid), pH 10.0]; (iii) enzyme; and (iv) distilled water added for a final volume of 6.0 mL. Enzymatic assays were conducted at a temperature of 37° C. The fatty acids formed during the hydrolytic enzymatic reaction were extracted with an organic solvent and titrated following the procedure described in U.S. Pat. No. 4,283,494.

A quantity of the lipase of the invention was used to determine its molecular weight. The molecular weight of the lipase of *P. alcaligenes* was found to be about 88,000 using gel filtration chromatography and comparing the retention time of the lipase with molecular weight calibration standards.

(C) Laundering Effectiveness of *P. alcaligenes* SD2 And Dodecylbenzene Sulfonate Laundering effectiveness of SD2 lipase was evaluated in a standardized procedure adapted from one disclosed in European Patent Application 0214761 #86306091.9 (6/8/86), incorporated herein by reference in its entirety. The ingredients in the laundering solution and the procedure followed in the laundering protocol are described below.

Laundering Solution (a) 0.2M Tris HCl, pH 8.5
(b) Lipase, 5 units/mL (determined at pH 8.5, 30° C.)
(c) Surfactant, 0.05% (w/v) sodium dodecylbenzene sulfonate based upon the volume of the laundering solution
(d) Water added to provide a final solution volume of 10.0 mL

Laundering Protocol

The tests were conducted at 40° C. for the times indicated. Cleaning efficacy was determined by measuring the amount of fatty acids produced as a result of triglyceride hydrolysis, expressed as a percentage of available fatty acids added as triglyceride to the fabric. Triglyceride stained fabric is prepared by adding 0.5 mL of a 3.0% (v/v) lard oil in chloroform solution to each side of a 2"×3" swatch of No. 400M Mercerized white cotton fabric (Testfabrics, Inc., Middlesex, N.J.).

The stained cloths are cut into 8 similar size pieces then placed in 25×150 mm test tubes containing the laundering solution. For the 15-minute surfactant exposure, the laundering proceeds for 60 minutes in the presence of the enzyme before surfactant is added and laundering is continued for an additional 15 minutes. The surfactant is present throughout the 75 minutes of laundering in the 75-minute test. The tubes are agitated on a vortex mixer for 10 seconds every 5 minutes for the duration of the test. After completion of the laundering period, samples of the laundering solution are taken for fatty acid analysis which is performed using the NEFA-C test kit produced by Wako Pure Chemical Industries, Ltd. (Osaka, Japan). Previous tests have shown this test kit procedure is not interfered with by the ingredients of the laundering solution at the concentrations used.

The results in terms of cleaning efficacy for two trials, using two different batches of SD2 lipase were compared against the results obtained using similar amounts of NOVO Lipolase ™, a commercial lipase intended for use as a laundering detergent additive. With SD2 lipase, cleaning increased with time of surfactant exposure. In contrast, cleaning decreased with exposure to the surfactant in the case of NOVO Lipolase. Percent cleaning ranged from 13% to 23% in the "15-minute test" using SD2 lipase to 22% to 35% cleaning in the "75-minute test." By contrast, NOVO Lipolase exhibited no better than 8% cleaning in the "15-minute test" and 2% to 3% in the "75-minute test."

Based upon the above results, it is clear that SD2 lipase is effective in removing triglyceride stains from cotton fabric in the presence of the commonly used dodecylbenzene sulfonate surfactant at a concentration of the latter that is commonly encountered in laundering. SD2 lipase is clearly superior to NOVO Lipolase in these comparisons and, on the basis of these results, would be expected to outperform NOVO Lipolase in formulations containing this anionic surfactant.

What is claimed is:

1. A detergent composition comprising the microbial lipase SD2 and dodecylbenzene sulfonate, wherein said lipase is present in an amount of between about one million and about 100 million lipase units per kilogram of dodecylbenzene sulfonate in the detergent composition, and wherein said dodecylbenzene sulfonate is present in an amount of between about 0.01 and about 20 weight percent based upon the total weight of said detergent composition.

2. The detergent composition of claim 1 wherein said lipase SD2 is characterized by having (i) an optimum pH for activity of about $8 \pm 0.5$; (ii) an optimum temperature for activity of about 30° to 55° C. and (iii) a molecular weight as measured by gel permeation chromatography of about $8.8 \times 10^4$.

3. The detergent composition of claim 1 wherein said lipase is present in an amount of between about 5 million and about 10 million lipase units per kilogram of dodecylbenzene sulfonate in the detergent composition.

4. In an improved detergent composition comprising dodecylbenzene sulfonate, the improvement comprising said detergent additionally containing the microbial lipase SD2 in a cleaning effective amount of between about one million and about 100 million lipase units per kilogram of dodecylbenzene sulfonate in the detergent composition, said dodecylbenzene sulfonate being present in an amount of between about 0.01 and about 20 weight percent based upon the total weight of said detergent compositon.

5. A laundry wash solution comprising water, dodecylbenzene sulfonate and the microbial lipase SD2, said dodecylbenzene sulfonate being present in a cleaning effective amount of between about 0.01 and about 20 weight percent based upon the total weight of said wash solution and said lipase being present in said wash solution in an amount of between about 1 and about 500 lipase units per milliliter of wash solution.

6. The laundry wash solution of claim 5 wherein said lipase is present in said wash solution in an amount of between about 3 and about 5 lipase units per milliliter of wash solution.

* * * * *